(12) United States Patent
Poulsen

(10) Patent No.: US 10,835,303 B2
(45) Date of Patent: Nov. 17, 2020

(54) DEVICE FOR THERMAL ABLATION

(71) Applicant: KEBOMED AG, Root Langenbold (CH)

(72) Inventor: Henrik Bisgaard Poulsen, Slangerup (DK)

(73) Assignee: KEBOMED AG, Root Langenbold (CH)

( * ) Notice: Subject to any disclaimer, the term of this patent is extended or adjusted under 35 U.S.C. 154(b) by 1082 days.

(21) Appl. No.: 14/896,330

(22) PCT Filed: Jun. 6, 2014

(86) PCT No.: PCT/EP2014/061893
§ 371 (c)(1),
(2) Date: Dec. 4, 2015

(87) PCT Pub. No.: WO2014/195489
PCT Pub. Date: Dec. 11, 2014

(65) Prior Publication Data
US 2016/0120585 A1     May 5, 2016

(30) Foreign Application Priority Data

Jun. 7, 2013  (DK) .............................. 2013 70312
Apr. 29, 2014  (DK) .............................. 2014 70263

(51) Int. Cl.
*A61B 18/04*     (2006.01)
*A61M 25/10*     (2013.01)
(Continued)

(52) U.S. Cl.
CPC .............. *A61B 18/04* (2013.01); *A61B 17/42* (2013.01); *A61B 18/082* (2013.01);
(Continued)

(58) Field of Classification Search
CPC ....... A61B 18/04; A61B 18/08; A61B 18/082; A61B 2018/00517; A61B 2018/00547;
(Continued)

(56) References Cited

U.S. PATENT DOCUMENTS 5,155,965 A * 10/1992 Tabei .................. E04G 23/0211
52/742.16
5,190,540 A     3/1993 Lee
(Continued)

FOREIGN PATENT DOCUMENTS

EP     0 555 900 A1     8/1993
EP     0 873 723 A2    10/1998
(Continued)

*Primary Examiner* — Michael F Peffley
*Assistant Examiner* — Samantha M Good
(74) *Attorney, Agent, or Firm* — Muncy, Geissler, Olds & Lowe, P.C.

(57) ABSTRACT

The invention provides a device for thermal ablation at a site in a subject. The apparatus comprises an expandable bladder; a displacement chamber having a variable volume; an elongated catheter forming fluid communication between the bladder and the displacement chamber; and a heater for heating the fluid. To obtain an improved pressure control and a reliable structure, the chamber comprises a syringe structure including a piston movable in a cylinder by power driven means for varying the volume of the displacement chamber.

15 Claims, 11 Drawing Sheets

(51) Int. Cl.
*A61B 17/42* (2006.01)
*A61B 18/08* (2006.01)
*A61B 18/00* (2006.01)
*A61B 17/00* (2006.01)
*A61B 90/00* (2016.01)

(52) U.S. Cl.
CPC  *A61M 25/10182* (2013.11); *A61M 25/10185* (2013.11); *A61B 2017/00557* (2013.01); *A61B 2017/4216* (2013.01); *A61B 2018/0022* (2013.01); *A61B 2018/0091* (2013.01); *A61B 2018/00517* (2013.01); *A61B 2018/00559* (2013.01); *A61B 2018/00577* (2013.01); *A61B 2018/00714* (2013.01); *A61B 2018/00744* (2013.01); *A61B 2018/046* (2013.01); *A61B 2090/032* (2016.02); *A61B 2090/064* (2016.02)

(58) Field of Classification Search
CPC ........... A61B 2018/00559; A61B 2018/00577; A61M 25/1018; A61M 25/10182; A61M 25/10185
See application file for complete search history.

(56) References Cited

U.S. PATENT DOCUMENTS

| | | | |
|---|---|---|---|
| 2002/0151882 A1* | 10/2002 | Marko | A61B 18/08 606/28 |
| 2004/0267340 A1* | 12/2004 | Cioanta | A61F 7/123 607/105 |
| 2005/0288660 A1 | 12/2005 | Ryan et al. | |
| 2007/0066990 A1 | 3/2007 | Marsella et al. | |
| 2010/0004534 A1* | 1/2010 | Neer | A61M 5/145 600/432 |
| 2010/0043802 A1 | 2/2010 | O'Brien et al. | |

FOREIGN PATENT DOCUMENTS

| | | |
|---|---|---|
| EP | 0 873 723 A3 | 1/2000 |
| WO | WO 01/64120 A1 | 9/2001 |
| WO | WO 03/054660 A2 | 7/2003 |
| WO | WO 03/054660 A3 | 8/2003 |
| WO | WO 2009/039038 A1 | 3/2009 |

\* cited by examiner

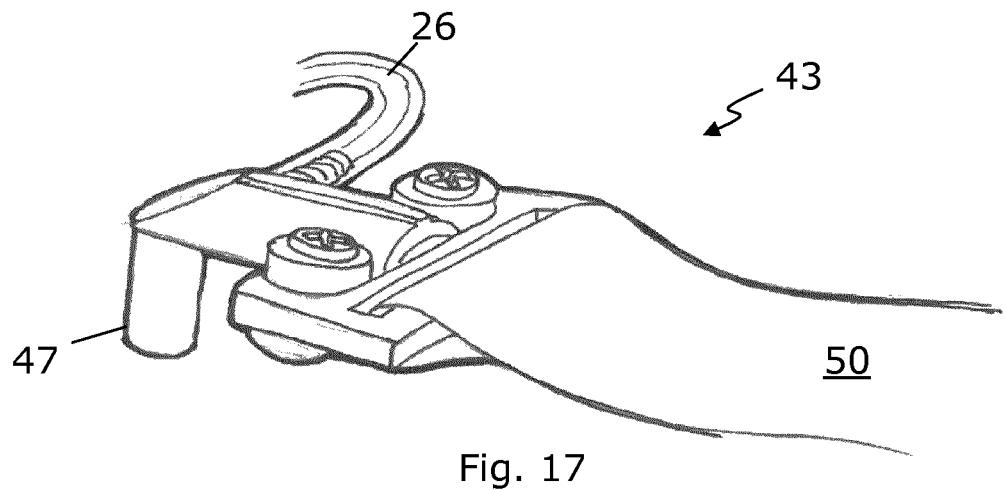
Fig. 17
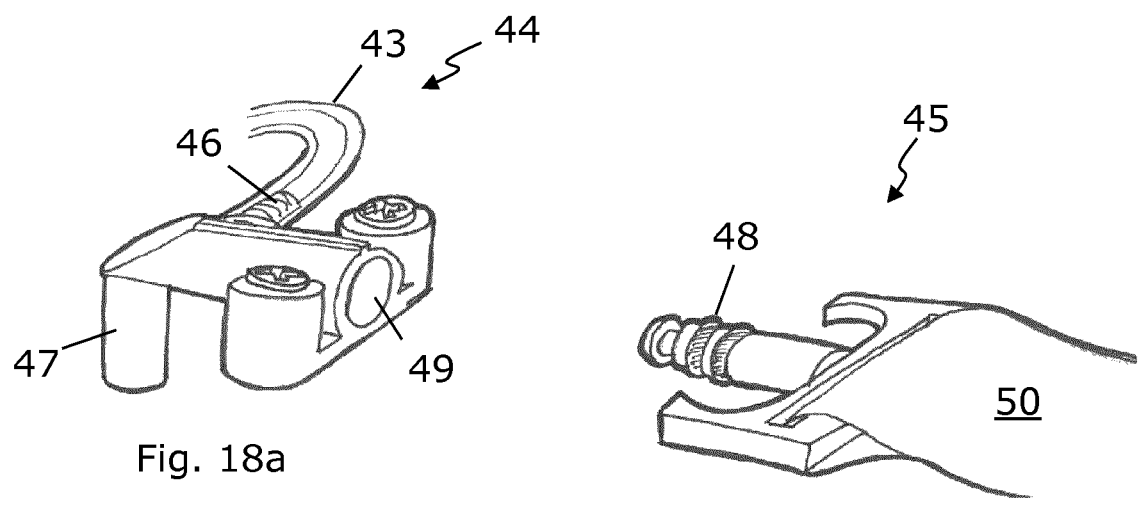
Fig. 18a
Fig. 18b

DEVICE FOR THERMAL ABLATION

FIELD OF THE INVENTION

The invention relates to a device for thermal ablation at a site in a subject. Particularly, the invention relates to a device comprising a fluid contained in a reservoir, where the reservoir comprises an expandable bladder; a displacement chamber having a variable volume; and an elongated catheter forming fluid communication between the bladder and the displacement chamber. The device further comprises a heater for heating the fluid.

DESCRIPTION OF RELATED ART

Application of thermal energy is known for treating body tissues. Particularly, it is well known to effect necrosis of the endometrium e.g. by use of an expandable balloon filled with a fluid at an elevated temperature, typically about 80-90° Celsius.

In an unexpanded state, the balloon is inserted into uterus of the subject and hot fluid is displaced into the balloon which thereby expands. Close contact between the hot outer surface of the balloon and the tissue lining for which necrosis is desired is maintained typically for 8-15 minutes after which the fluid is drained from the balloon. The collapsed balloon can finally be removed from the subject.

In some devices, the fluid is preheated outside the body and then displaced into the balloon. In another type of device, the balloon houses a heater which can heat the fluid once it is inside the balloon.

The heating of the fluid and the displacement into and out of the balloon require monitoring by the medical practitioner. If the balloon is filled too much, too fast, or with a fluid which is too hot, it may have detrimental effect on the subject.

SUMMARY OF THE INVENTION

It is an object of embodiments of the invention to improve the existing methods and devices for conducting thermal ablation and particularly to provide a more simple and reliable device which facilitates improved pressure and temperature control, improved monitoring, and reduced system costs.

According to a first aspect, the invention provides a device according to claim 1.

The use of a power driven syringe facilitates in a simple manner, an exact displacement of the fluid into the bladder and thus controlled expansion of the bladder.

Before removal of the bladder from uterus, the bladder is deflated by removal of the fluid. For this purpose, the syringe structure is operable in both directions, i.e. both for reduction and expansion of the chamber volume, and the reservoir is completely sealed. This may ensure complete emptying and collapsing of the bladder and thus more simple removal of the bladder from the uterus after the treatment is finished.

The term Completely sealed herein means that the reservoir is liquid and optionally also gas tight, e.g. gas tight enough to prevent intrusion of air during increasing of the volume of the displacement chamber and tight enough to prevent escape of the fluid during reduction of the volume of the displacement chamber. In one embodiment, the reservoir comprises no openings into the internal space in the reservoir, and in another embodiment, the reservoir only comprises openings which can be sealed in a liquid or gas tight manner. The reservoir may e.g. be sufficiently tight to resist a pressure of a liquid or a gas of at least 1.5 times the external pressure outside the reservoir, or to resist a pressure of at most 0.75 times the external pressure.

The power driven means may work on the cylinder or on the piston to move that element relative to the other element of the syringe structure. Particularly, the combination between power driven means and a syringe structure enables precise dosing of fluid into the bladder by use of very simple and cheap motors and thereby enables fine adjustment of the pressure in the bladder.

Relative displacement of the cylinder and piston may e.g. be effected by a worm shaft etc. or it may generally be based on a threaded engagement between a driven and a driving element, e.g. between a nut which is rotated by the motor and therefore constitutes the driving element and a threaded piston or threaded element connected to the piston and which thereby constitutes the driven element.

The catheter may be connected to one of the piston and cylinder, and the motor could be arranged to move the other one of the piston and cylinder relative thereto.

The power driven means could particularly be constituted by a rotary motor of the kind including a rotor and a stator, e.g. a DC motor, e.g. a step motor. Alternatively or additionally, the power driven means may include electromechanical actuation means, e.g. in the form of a solenoid operating to move the piston and cylinder relative to each other.

The syringe and optionally also the heater and/or an electronic control system for controlling operation of the syringe and heater may be driven by a power driven means which is independently powered. Herein, independent powering means that the device contains a local source of electrical energy, in the following simply referred to as a battery.

By the term "battery" is herein meant a number of cells, e.g. 1, 2, 3, 4 or more cells, each capable of delivering electrical power. Particularly, the battery may comprise at least one electrochemical cell and/or at least one capacitor.

The battery may typically deliver between 3 and 20 volt and have about 500-2600 mAH of capacity. It may be for disposable, one time usage or it may be rechargeable for multiple usages.

Particularly, it is an object to make a completely independent, single piece device for single use. Typically, however, batteries should be disposed in containers specifically for receiving batteries, and typically, instruments which may have been contaminated with biological material such as blood and tissue should be disposed in other containers specifically for that purpose. It may therefore be an advantage if the device comprises a detachable independent powering means designed for intended destruction by which the battery, capacitor, or similar power source becomes detached from the chassis such that reassembly becomes difficult or impossible.

The bladder may be pre-shaped e.g. to approximate the bicornual shape of the uterus. It may be manufactured from bio-compatible, non-allergenic material, and it may come in different sizes, e.g. in two pre-shaped sizes; one for nulliparous uteri and one for parous uteri. The bladder may also have completely different shapes for non-endometrial balloon ablation, e.g. for prostatic treatment etc.

The bladder could be made from an elastically deformable rubber, silicone or latex material. In one embodiment, the bladder comprises at least a first and a second balloon positioned one within the other to increase safety if one balloon should be ruptured.

In one embodiment, the bladder comprises a first and a second balloon, one within the other, and the fluid is injectable between the two balloons, i.e. the space between the first and second balloon forms part of the reservoir. In this embodiment, the inner balloon may be expanded e.g. by air. Since it is only the space between the first and second balloon which is filled with the fluid, the amount of fluid which is necessary for a treatment can be reduced whereby the thermal capacity of the system is reduced. This reduces also the necessary thermal energy for bringing the fluid to the requested temperature and the time it takes to heat the fluid. As a further advantage, the fluid cools down faster and the risk of unintended burns is reduced.

The heater may e.g. be incorporated in, or it may form part of the cylinder or piston. In this way, relative movement between the cylinder and piston causes also relative movement between the heater and one of the cylinder and piston. This may increase the thermal convection and facilitate a more homogeneous temperature of the fluid in the chamber.

The inflation medium may particularly be heated to a temperature above 100° C. and more particularly to a temperature above 130° C. such as to a temperature in the range of 120-150° C. or to a temperature in the range of 120-160° C. To reach this temperature, the inflation medium may particularly be a liquid with a boiling point above 150° C. and preferably even above 200° C. The inflation medium may particularly be glycerol, e.g. $C_3H_8O_3$.

Further, the balloon may desirably be made from a material which resists temperatures above 150° C., or above 200° C., and desirable be made from a material which exposes at most 5 percent change in module of elasticity during a temperature increase from 20° C. to 150° C., where the module of elasticity is defined as a tendency to be deformed elastically—i.e., non-permanently—when a force is applied to it.

This relatively high temperature may reduce the duration of the treatment but may introduce a risk of damaging the cervix and vaginal tissue lining. To prevent such damages, the entire catheter, or at least an insertable part thereof, or at least the proximal end, may preferably be made such that the thermal spreading from the inner surface of the catheter to the outer surface of the catheter is low.

Herein, proximal end is defined as that end where the bladder is attached, i.e. the end pointing towards the patient during treatment. The distal end is the opposite end pointing away from the patient. Likewise, the proximal direction is the direction towards the patient and distal direction is the direction away from the patient during treatment.

The "insertable part" is herein defined as that part of the catheter which, during use of the device, is inserted into the body of the treated subject, i.e. e.g. into the vaginal canal or the cervical canal. The "proximal end" is herein defined as less than half of the length of the catheter at that end where the bladder is attached to the catheter, i.e. from the bladder and at most half way down, e.g. 1/3, or 1/4 of the way towards the proximal end of the catheter.

In one embodiment, the thermal conductivity of the insertable part or of the proximal end is lower than the remaining portion of the catheter.

In one embodiment, the entire catheter, the insertable part or the proximal end has a lower thermal conductivity than the bladder.

In one embodiment, the entire catheter, the insertable part or the proximal end has first and second coaxial elements extending about a conduit, the first and second elements have different thermal conductivity. Due to the different thermal conductivity, the propagation of thermal energy through the wall of the catheter may be reduced.

Particularly, one of the elements may have a thermal conductivity less than one tenth of the thermal conductivity of the bladder and/or less than one tenth of the thermal conductivity of the other element. One element could e.g. be made from steel, e.g. from titanium or stainless steel and the other element could be made from plastic. Preferably the outer element could be made from plastic while the inner element is made from steel.

Fibre composite materials typically have a low thermal conductivity. To prevent excessive temperatures on the outer surface of the catheter, the entire catheter, the insertable part, or the proximal end could be made from a fibre composite material, e.g. a glass fibre or carbon fibre reinforced polymer material.

The entire catheter, the insertable part, or the proximal end could be covered at least partly with a surface layer of a bio-compatible material, e.g. with a hydrophilic coating, PTFE (Teflon™), or simply coated with a layer of hydrogel. PTFE may provide an additional advantage since it has a very low thermal conductivity and it may therefore prevent high temperatures on the outer surface of the catheter.

To further prevent damages to the cervix and vaginal lining and/or to prevent unintended inflation of the bladder during heating of the fluid, the syringe structure may be activated to increase the volume of the displacement chamber while the fluid is heated. In this way, the device may compensate for an increase in volume of the fluid caused by heating, and unintended propagation of the hot fluid from the displacement chamber into the catheter or even into the bladder during heating can be prevented. By this feature, the fluid may be heated without any inflation in a first step, and subsequently, the bladder can be inserted into the uterus in a completely deflated, however, fully heated state. As a result, the patient is firstly involved when the fluid is hot, and at this point in time, the device can be inserted directly into the uterus since the bladder remains unexpanded.

The activation of the syringe structure to increase the volume of the displacement chamber could e.g. be controlled based on the temperature of the fluid or based on a pressure of the fluid or based on combinations there between.

The device may include a safety feature which reacts, e.g. by stopping continued treatment, if the fluid is heated without the need to compensate for pressure changes The safety feature may e.g. react if the fluid id heated and no compensation is required, e.g. if the fluid is heated without an increased pressure in the reservoir has been detected.

As an alternative, or for emergency purpose, e.g. if the power driven means fails, the device may comprise an emergency exit allowing fluid to be drained from the reservoir and thus allowing collapsing of the bladder without operating the power driven syringe structure.

To avoid spillage of the fluid and to avoid potential scalds caused by the hot fluid, the device may comprise a liquid absorbing material arranged to receive the fluid which is drained through the exit. The liquid absorbing material may e.g. include a hydrophilic material, e.g. including polyvinylidone (PVP) or other materials well known for their liquid absorbing properties.

The emergency exit may be sealed by an emergency valve structure, e.g. a manually operable valve.

To prevent reuse of the device, the emergency valve structure may be operable from a closed position to an open position, but not reversible to the closed position. I.e. once opened, the fluid will drain out of the reservoir and the reservoir will remain open whereby the device becomes unsuitable for further use.

The device may comprise at least one sensor capable of determining temperature or pressure in the reservoir. As an example, the device may comprise separate sensors for sensing temperature and pressure. The device may also comprise several sensors capable of sensing temperature and/or several sensors capable of sensing pressure, and control logic capable of reading several pressure and/or temperature signals from the sensors and to determine a fault situation in case the difference between the signals from two identical sensors are above a limit value.

E.g. to increase safety or to increase simplicity of the device in use, at least one timer capable of determining a duration of the treatment may be included. The timer may trigger reduction of the volume of the displacement chamber.

Accordingly, the timer function determines a duration in which the bladder is inflated, and after a fixed duration or after a duration which can be set by the user, the control system is programmed to increase the volume and thus to deflate the bladder, alternatively to activate the emergency exit. In that way, the risk of detrimental effects caused by too lengthy treatment can be avoided. The timer may be adjusted based on an actually determined temperature of the fluid such that the duration of the treatment is adapted to an actually achieved temperature.

The operation may be as follows:

1. The user initiates the treatment by turning on the device. By this activity, heating may begin—alternatively, the heating begins when the start button is pressed, c.f. step 3 below.

2. The bladder is inserted to the site of operation, e.g. into a body cavity such as the uterus for endometrial thermal ablation.

3. When the bladder is in correct position, the user may initiate the treatment by pressing a start button. This activity will cause the piston to move relative to the cylinder whereby the volume of the displacement chamber becomes reduced. At the same time, a timer is initiated.

4. After a predetermined duration, the piston moves back to its initial position relative to the cylinder whereby the fluid is drained from the bladder. In this procedure, the completely sealed reservoir enables complete collapsing of the bladder. Alternatively, the draining of the bladder is initiated manually by activation of a stop button, or the fluid is drained through the emergency exit.

When the bladder is drained, it may be removed from the operation site and the treatment is finished.

The device may comprise an electronic control system configured for fully automatic operation of the device. I.e. the control system may be configured to control the syringe structure through the power driven means, and to control the heater. For this purpose, the control system communicates with the power driven means for controlling positioning of the piston relative to the cylinder. Particularly, the control system may be configured to control the positioning of the piston relative to the cylinder based on a signal communicated with at least one of the at least one sensors.

The electronic control system may particularly be programmable to allow redefinition of the treatment process e.g. by amending temperatures, pressures, and/or duration of the treatment.

To ensure only one-time usage of the device and disposal of the device after use, the control system may be configured to control the positioning of the piston relative to the cylinder such that the volume of the chamber can be reduced only one time, and subsequently increased only one time. In that way, the risk of contamination by use of a previously used device can be avoided.

The at least one sensors could be incorporated in, or form part of at least one of the piston and the cylinder.

To reduce the risk of the bladder being released from the catheter and thereby potentially being left in the uterus, the catheter may be formed in one piece with the bladder. In a similar manner, the catheter may be formed in one piece with one of the cylinder and the piston.

To prevent damaging the bladder during insertion of the catheter into a body cavity such as uterus, the device may comprise a transition body forming a distal termination of the catheter and located inside the bladder. The transition body is softer than the catheter such that it easily deforms and flattens out when reaching the bottom wall of the body cavity into which the bladder is inserted.

Herein, softer is defined as "obtaining a certain degree of elastically deformation by a lower pressure".

To seal the body cavity during the thermal ablation procedure, e.g. to seal uterus, the device may comprise a sealing member forming a protrusion on an outer surface of the catheter. The sealing member may e.g. be made from a soft, i.e. easily elastically deformable, polymer material, e.g. a hydrophilic material, e.g. a material containing acrylamide, polyvinylidone or other hydrophilic materials prepared such that they swell.

Particularly, the sealing member may extend circumferentially on an outer surface of the catheter, and it may particularly be made to expand upon contact with the fluid contained in the reservoir. In that way, leakage of the hot and potentially damaging fluid e.g. from uterus to the cervical or vaginal canal, e.g. if the bladder is ruptured, can be prevented. The sealing member may form one or more stripes circumferentially about an outer surface of the catheter, e.g. made by coating the outer surface of the catheter with a hydrophilic materiel.

The sealing member could be slidable axially along the outer surface of the catheter to thereby enable positioning of the sealing member at a distance from the tip of the catheter which corresponds to the depth of uterus.

When the catheter is inserted e.g. through cervix, the hydrophilic coating may swell upon absorption of body fluids, but particularly, it may swell upon leakage of the fluid from the reservoir if the bladder is ruptured. When the sealing body is swelled, it may provide a seal between the cervical canal and the catheter.

In one embodiment, the apparatus comprises powering means configured to power the heater by a pulsating electrical signal causing a cyclically repeated increase and decrease of the temperature of the heater.

Due to the pulsating electrical signal causing a cyclically repeated increase and decrease of the temperature of the heater, it has been found that the temperature of the inflation medium increases rapidly, and the increased temperature may become more equally distributed to thereby create less temperature variations over the surface of the distended bladder.

The heater could be configured to convert the electrical signal to thermal energy e.g. by use of ohmic resistance in one or more heating elements forming the heater or by use of ohmic resistance directly in the inflation medium or in the material of the bladder or by a combination between ohmic resistance in the inflation medium and in one or more heating elements.

The pulsating electrical signal may e.g. be provided by an electronic circuit forming control means for the device. The control means may communicate with the syringe structure and with the heater for regulating the inflation and heating. The control means could be configured to effect a pre-programmed sequence including the step of heating the inflation medium by use of a pulsating electrical signal while adjusting the pressure in the bladder, e.g. for keeping a constant pressure in the bladder to prevent inflation during heating.

The pulsating electrical signal could e.g. by a low frequency, 1-10 hertz, or a high frequency, 10 kHz-500 kHz, RF signal. The signal could also be a very low frequency signal, e.g. switching on/off in intervals of 1-20 seconds.

The catheter, the bladder, the displacement chamber, the heater could be joined inseparably to form integral parts of a mobile unit.

In a second aspect, the invention provides a method of expanding a bladder, the method comprising:
connecting the bladder by use of an elongated catheter to a displacement chamber having a syringe structure including a piston movable in a cylinder; and
using power driven means to vary the volume of the displacement chamber by relative movement of the piston and cylinder.

In different kinds of sterilisation techniques, heating of the device follows from the sterilisation. This is e.g. the case in different types of electron beam, gas, or vapour sterilisation. In ETO sterilisation processes taken as an example, regular temperatures are in the range of 25-55° C. and steam sterilisation raises the temperature even higher.

In a third aspect, the invention provides a method of manufacturing a device according to the first aspect of the invention.

The method comprises the step of using the power driven means to expand the volume of the chamber prior to, or during sterilisation of the device to thereby counteract volumetric expansion of the fluid caused by heating during sterilisation. Particularly, the compensation by increasing the size of the chamber may be combined with ETO sterilisation.

BRIEF DESCRIPTION OF THE DRAWINGS

FIGS. 17, 18a, 18b, 19, and 20 illustrate details of one embodiment of the emergency valve.

DETAILED DESCRIPTION OF AN EMBODIMENT

Further scope of applicability of the present invention will become apparent from the following detailed description and specific examples. However, it should be understood that the detailed description and specific examples, while indicating preferred embodiments of the invention, are given by way of illustration only, since various changes and modifications within the scope of the invention will become apparent to those skilled in the art from this detailed description.

Figure 1:
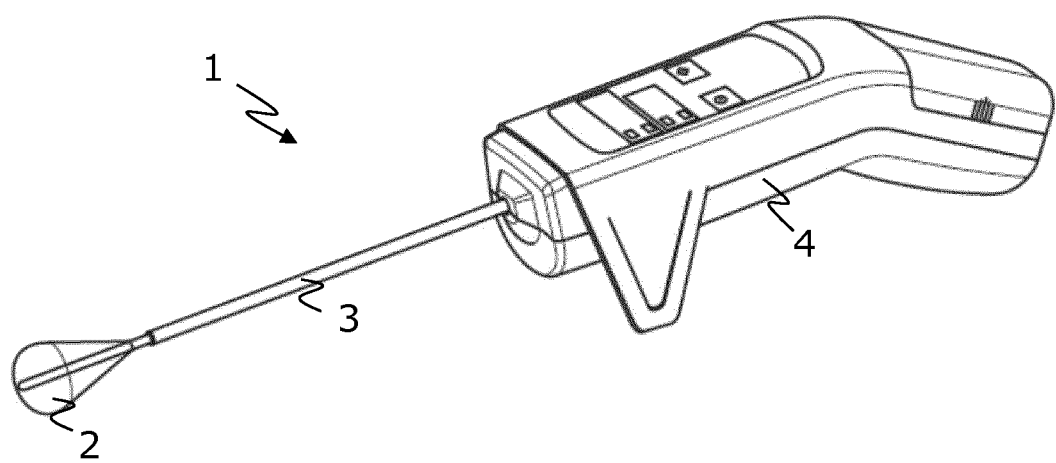
FIGS. 1 and 2 are perspective views of an assembled device according to the invention.
Figure 2:
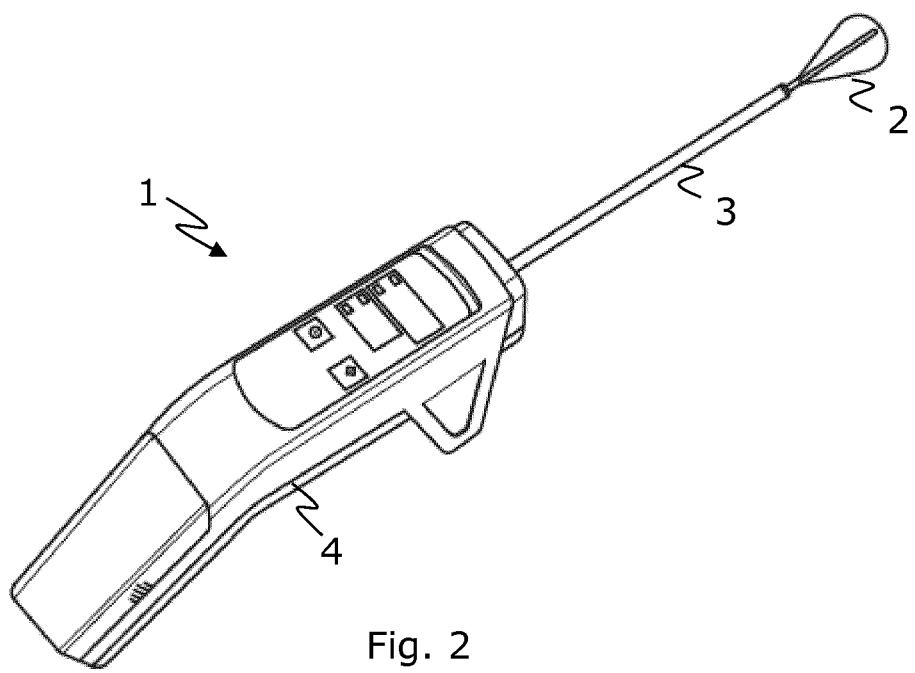

FIG. 1 illustrates a device 1 for effecting necrosis of the endometrium. The device comprises a fluid contained in a reservoir which is constituted by an expandable bladder 2 which is connected by an elongated catheter 3 to a displacement chamber (not shown) housed within the casing 4.

Figure 3:
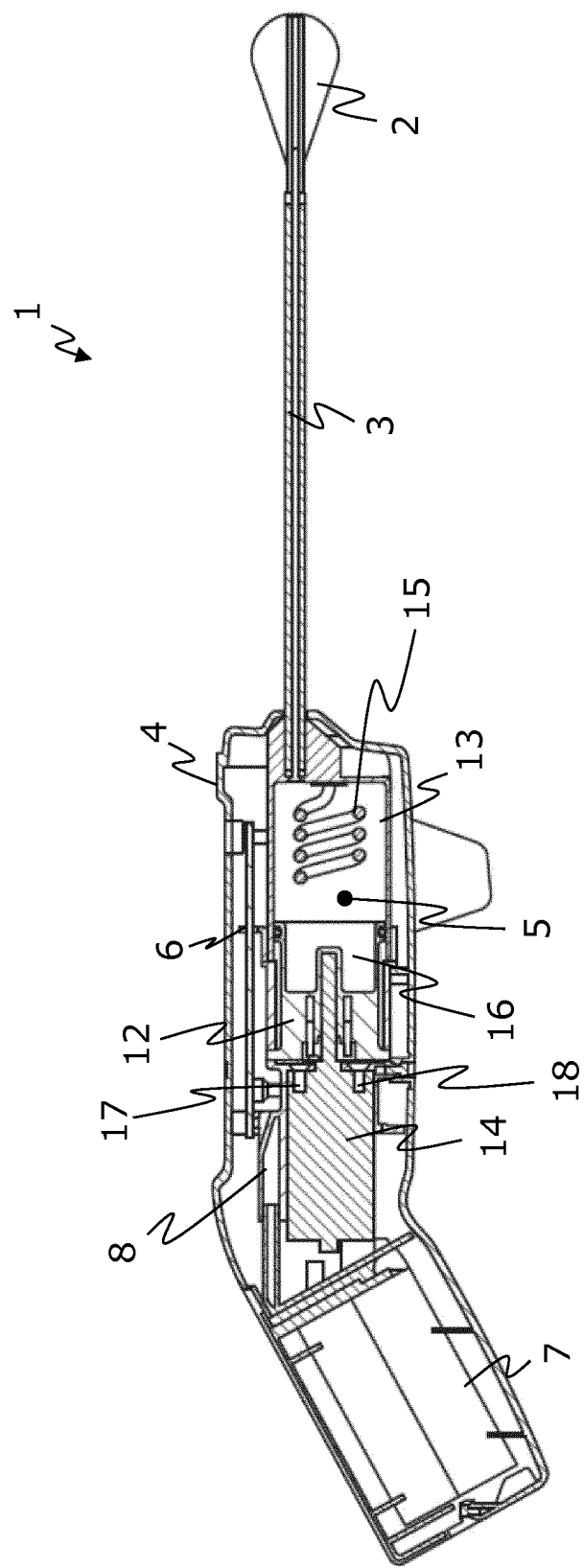
FIG. 3 is a side view, in cross section, of a device according to the invention.
Figure 4:
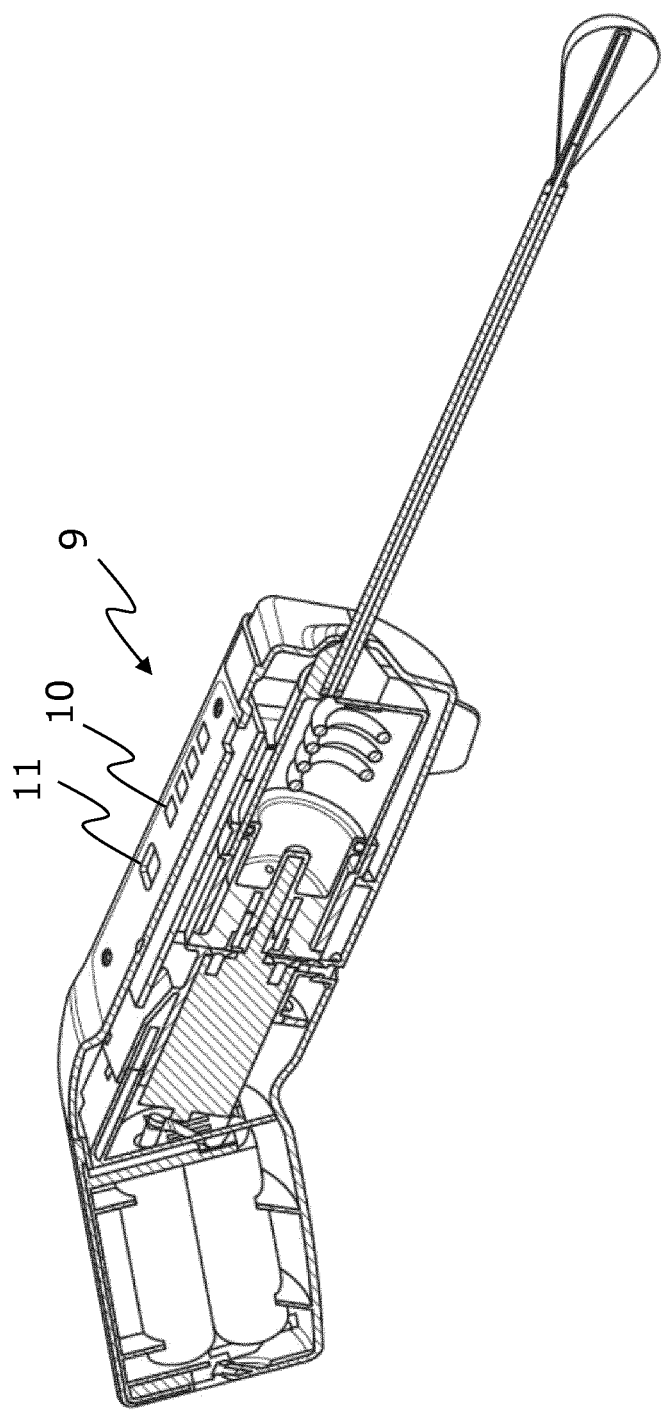
FIG. 4 illustrates details of the piston.

The casing is illustrated in a cross sectional view in FIG. 3. The casing houses the displacement chamber 5, a control system 6, a battery 7, a body 8 of a liquid absorbing material, and a user interface 9 (Cf. FIG. 4) including buttons 10 for controlling operation of the device and a display 11 for monitoring the temperature and/or the duration of the treatment.

The displacement chamber is constituted by a syringe structure including a piston 12 movable in a cylinder 13 by an electrical motor 14—in this case a DC servo motor or step-motor.

The control system may particularly provide a fully automatic system managing the entire treatment, i.e. the heating of the fluid, the expansion of the bladder, the duration in which the bladder is expanded and the collapsing of the bladder once the treatment is finished.

The control system may be integrated in a printed circuit board (PCB) which includes memory, a computer processing unit, and a program executable in the processing unit and configured to make the control system communicate with the heater, the motor, and/or with the sensors to carry out the process of:
heating the fluid until a predetermined temperature is achieved;
operating the motor until the bladder is inflated by the heated fluid;
counting a duration by a timer;
operating the motor until the bladder is deflated;
and notifying the user that the treatment is finished.

The control system may have storage means in which all data related to the treatment is stored. The control system may further have communication means adapted to provide documentation including data describing a treatment, e.g. the temperature, the duration, the pressure of the fluid and/or other data relevant for evaluating the treatment.

The heater 15 is attached to, and extends inside the cylinder 13. The piston forms a cavity 16 shaped and dimensioned to receive the heater 15.

When the piston is moved in the cylinder, the heater becomes received in cavity and the fluid therefore becomes displaced or "stirred" in the chamber in the vicinity of the heater 15. This increases the thermal convection and provides a more equal temperature in the fluid.

The device further comprises a sensor 17 capable of sensing pressure and a sensor 18 capable of sensing temperature of the fluid in the reservoir. The sensors communicate with the control system 6.

Figure 5:
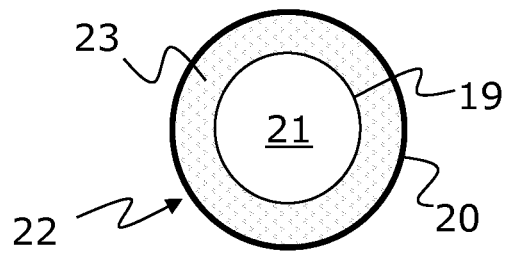
FIG. 5 illustrates details of the catheter in a cross sectional view.

FIG. 5 illustrates details of the catheter in a cross sectional view. The catheter comprises first and second coaxial elements 19, 20 extending about a conduit 21. The two elements are made from different materials and have different thermal conductivity to thereby reduce thermal spreading from the conduit to the outer surface 22 of the catheter. Between the coaxial elements 19, 20, the device may comprise a third element 23 having very low thermal conductivity. In one embodiment, the coaxial elements 19, 20 are in direct contact without the third element.

Figure 6:
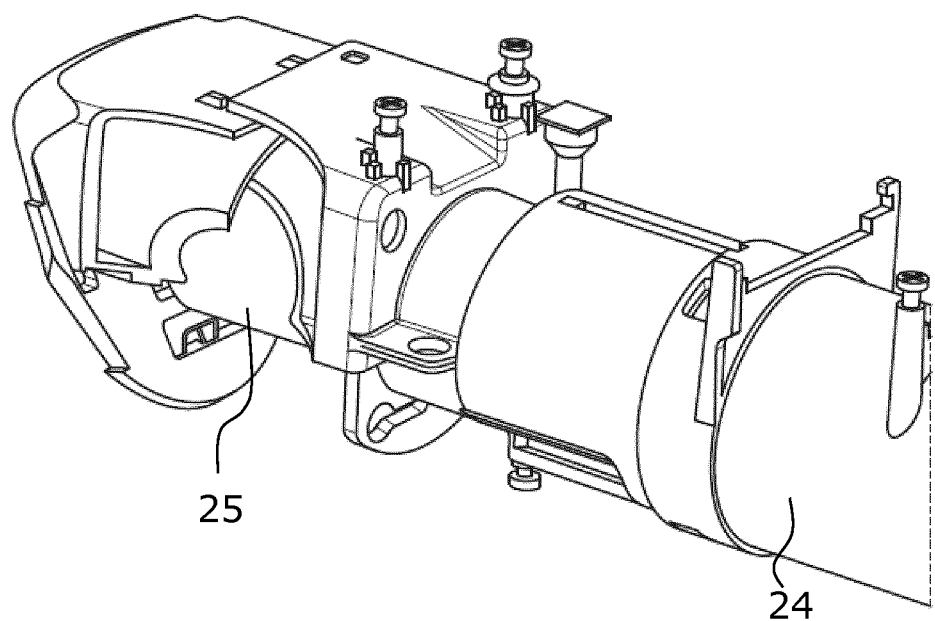
FIG. 6 illustrates details of the chamber.

FIG. 6 illustrates in a perspective view, the displacement chamber 24 and the motor 25 which constitutes the power driven means.

Figure 7:
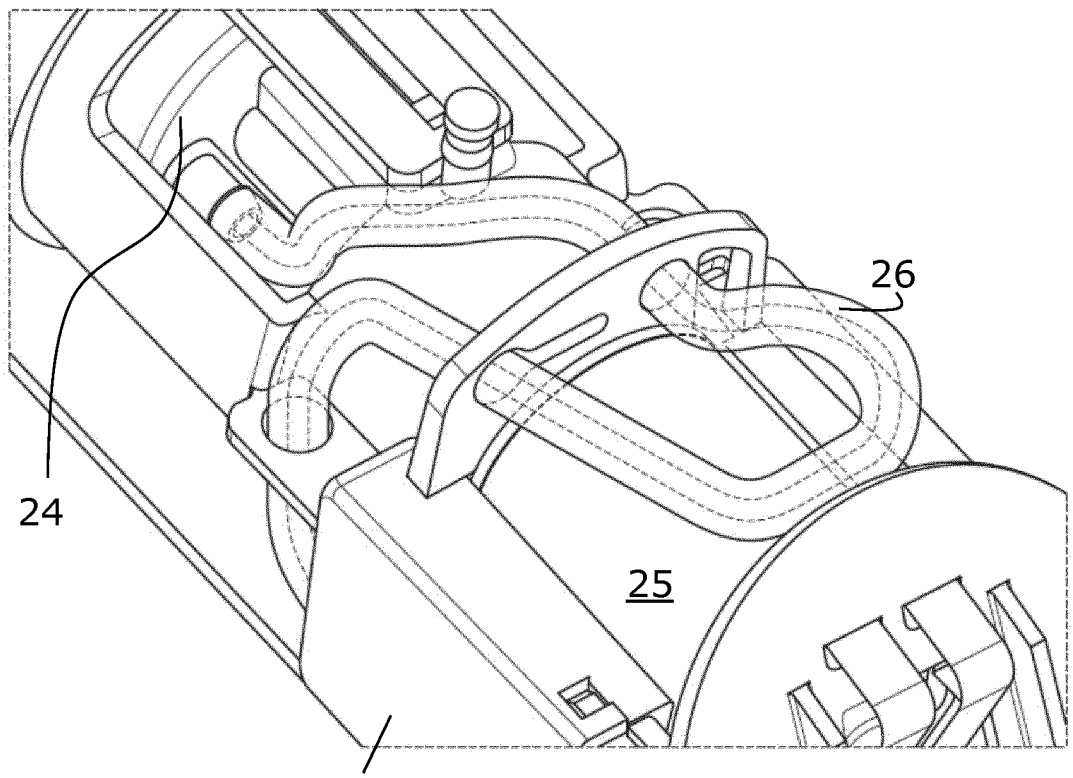
FIGS. 7 and 8 illustrate further details of the chamber.
Figure 8:
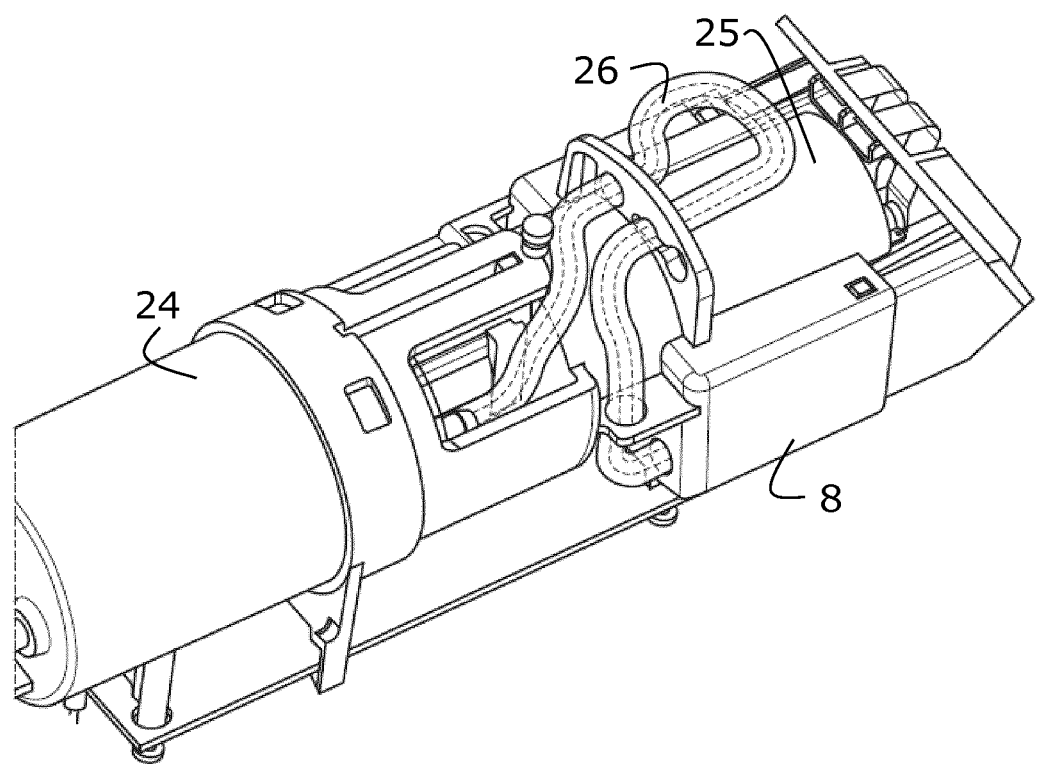

FIGS. 7 and 8 illustrate further details of the chamber 24. In this view, it is illustrated that the chamber comprises an emergency release structure 26 constituted by a rubber tube. The emergency release structure is in fluid communication with the disposal storage 8 which contains a liquid absorbing material. A valve 27 controls the drainage of inflation medium into the body 8. The emergency release structure is operated via the valve e.g. if the power driven means fails, e.g. when the battery is empty or in case of faults. In this embodiment of the emergency valve 27, the valve forms a passage for the rubber tube, and the passage has two dimensions. When the rubber tube is in one part of the passage, a small dimension squeezes the rubber tube and thereby prevents a fluid flow. When the rubber tube is in another part of the passage, a large dimension allows the rubber tube to open and thereby enables a fluid flow. The rubber tube may be configured to prevent permanent deformation in the squeezed state.

Figure 9:
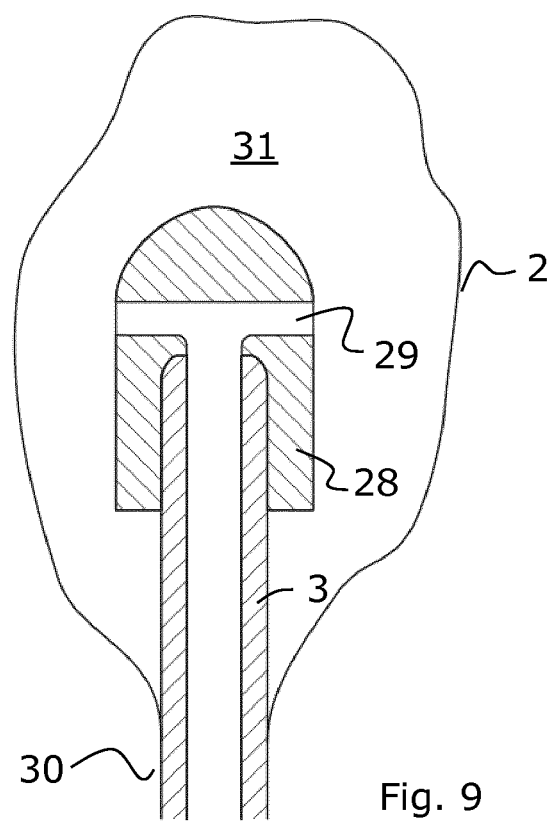
FIGS. 9-11 illustrate different embodiments of a transition body at the proximal end of the catheter inside the bladder.
Figure 10:
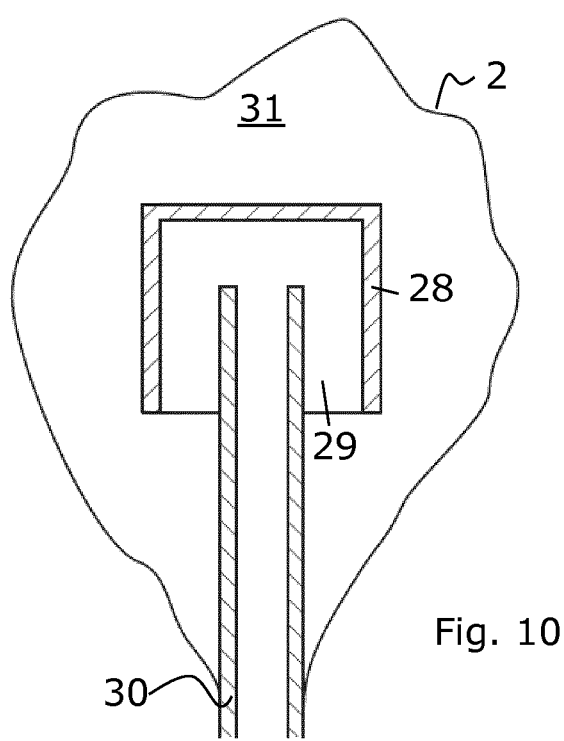
Figure 11:
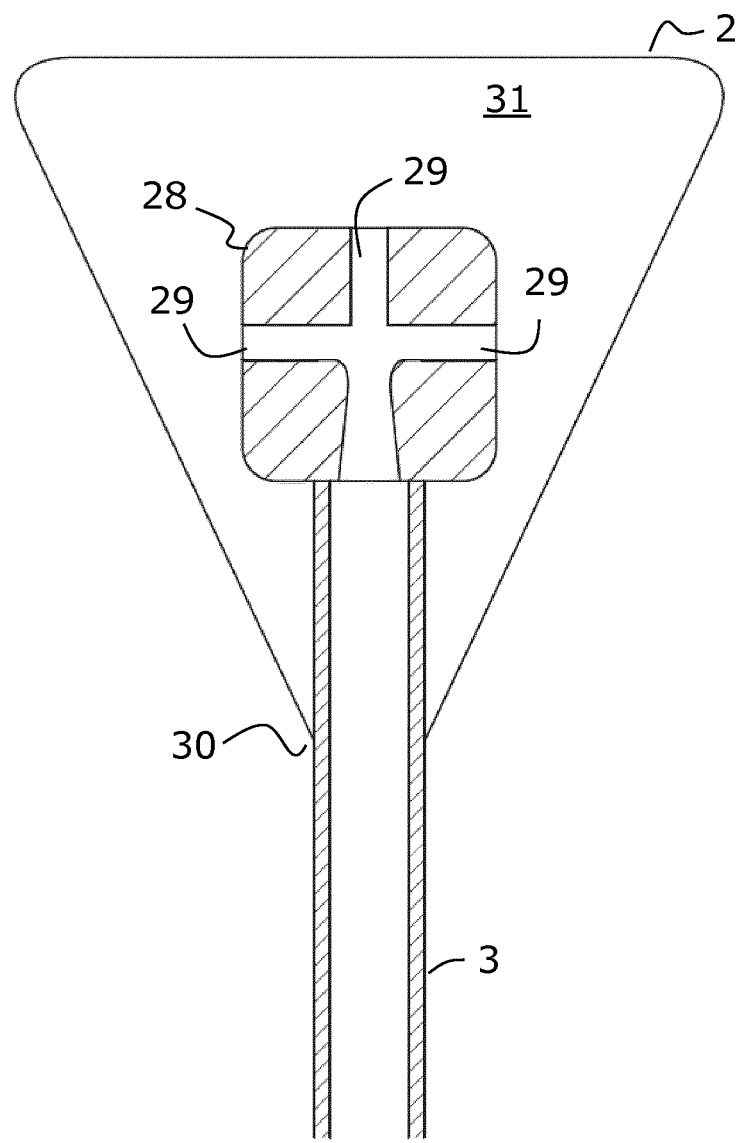
Figure 12:
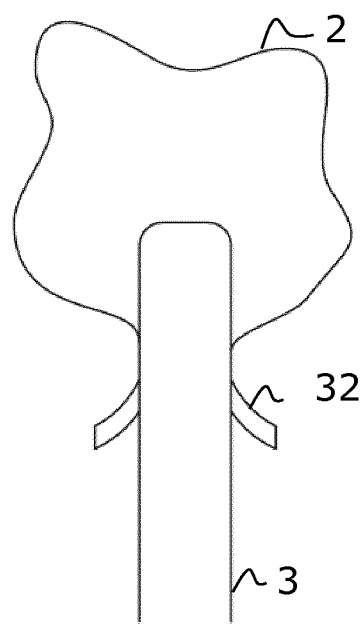
FIGS. 12-16 illustrate different embodiments of stop and sealing members.
Figure 13:
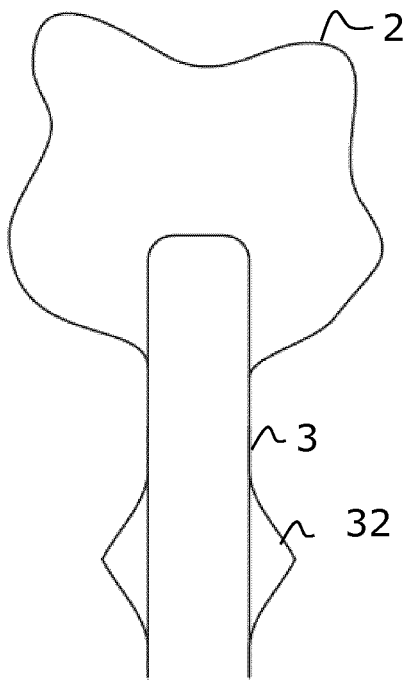
Figure 14:
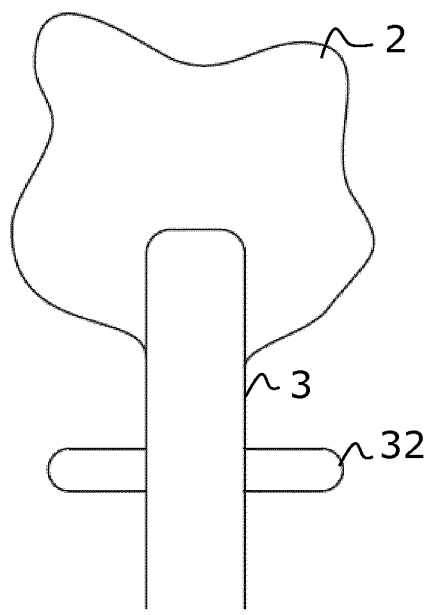
Figure 15:
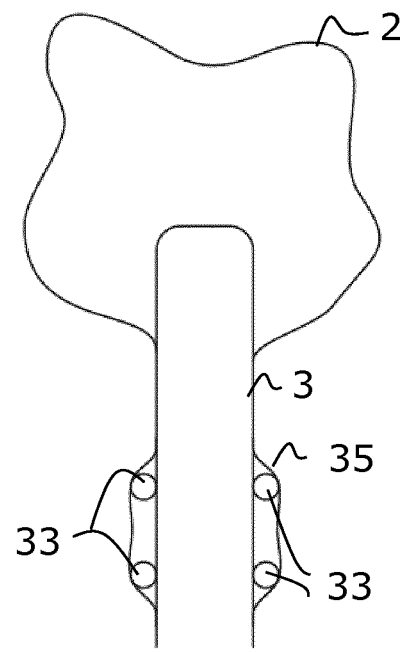

FIGS. 9-11 illustrate different embodiments of a transition between the elongated catheter 3 and the expandable bladder 2. The transition includes a transition body 28 of a very soft and resilient rubber, latex, silicone or similar soft material. The transition body is attached to the proximal end of the catheter 3 or it is formed by the proximal end of the catheter 3. During insertion of the bladder into a body cavity, e.g. the uterus, the transition body may come into contact with a rear wall of the body cavity whereby the user can feel that the full depth of the body cavity has been reached. Upon contact with the rear wall of the body cavity, the transition body is deformed and thereby protects the wall of the body cavity from damages and it protects the bladder to from being ruptured by a sharp tip of the catheter.

The transition body may include electronic sensing means configured to determine a distance to the rear wall or configured to determine impact between the transition body and the rear wall.

The transition body forms openings 29, e.g. sideways as illustrated in FIG. 9 or rearwards as illustrated in FIG. 10, or upwards as illustrated in FIG. 11. The openings allow the fluid to flow from the catheter into the bladder 2. Other softly rounded, bulbous shapes of the transition body may be used. The bladder 2 is adhesively attached to the outer wall 30 of the catheter 3 such that the transition body becomes included in the reservoir 31 inside the bladder.

FIGS. 12-15 illustrate different embodiments of stop and sealing members 32 for use of the device for endometrial ablation. The stop and sealing members cooperate with the cervix to provide a sealed passage of the catheter and bladder into the uterus. The embodiment illustrated in FIG. 15 includes two swellable bodies 33 located between an outer surface of the catheter and a sheath 35. When swelling, the swellable bodies presses the sheath against a surface of cervix and thereby seals the passage into uterus. The swellable bodies may e.g. be of a hydrophilic material.

Figure 16:
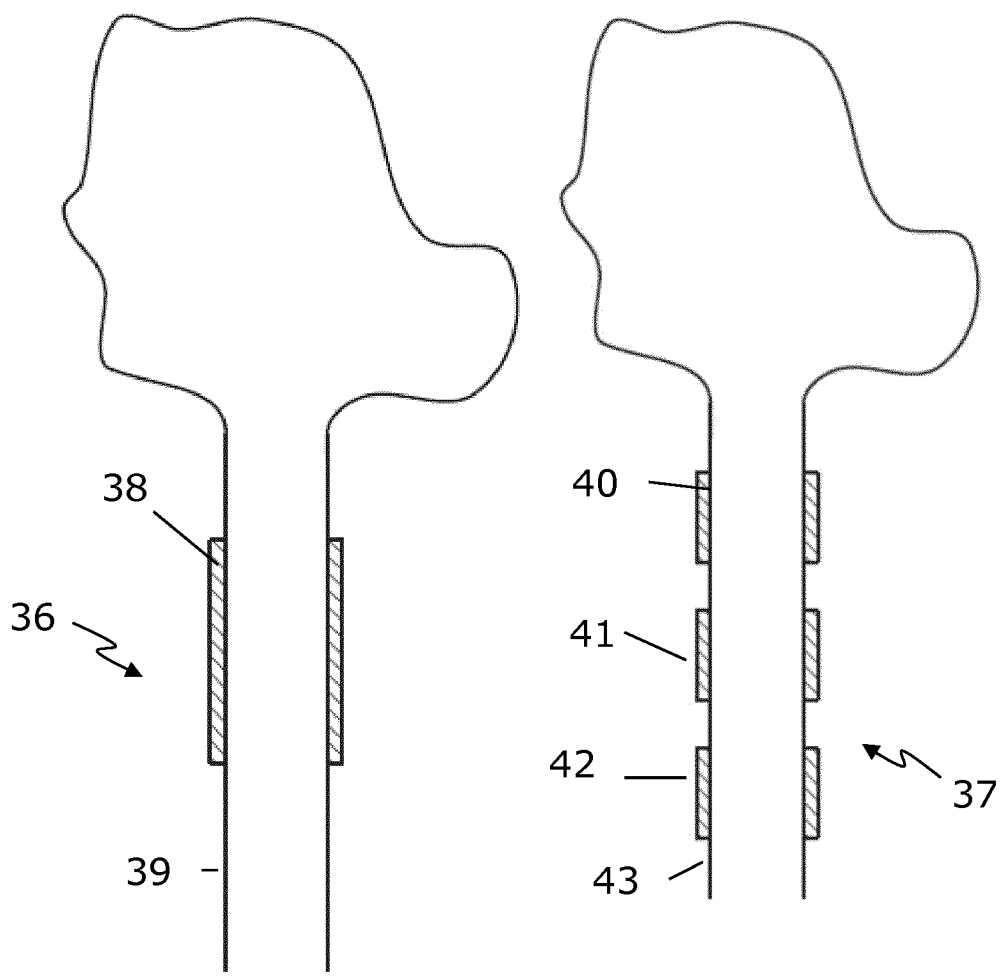
Figure 19:
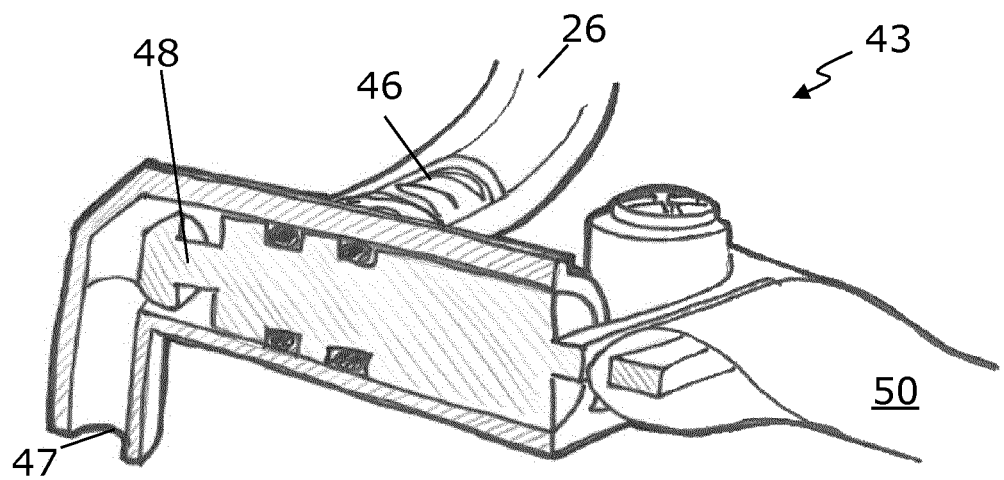
Figure 20:
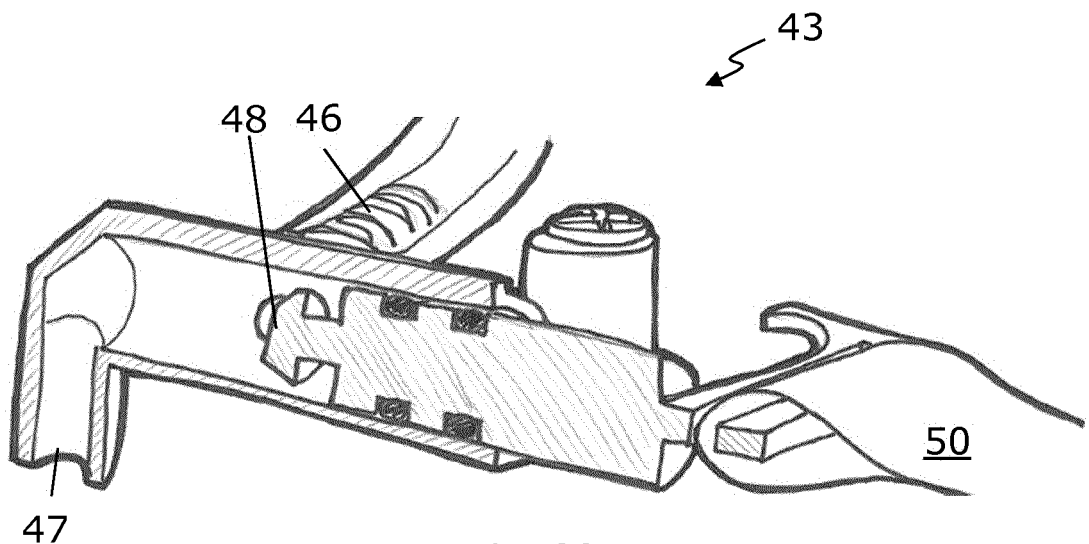

FIG. 16 illustrates two different catheters 36, 37. The catheter 36 has a single hydrophilic surface layer 38 provided as a coating about the body 39. The catheter 37 comprises three hydrophilic surface layers 40, 41, 42

FIGS. 17-20 illustrate details of another embodiment of the emergency valve 43 for the emergency exit 26, the exit and valve form an emergency release structure according to the invention.

The emergency valve controls a flow of the inflation medium into the disposal storage 8 or simply out of the apparatus. The emergency valve connects to the rubber hose 26 and comprises first and second valve parts 44, 45. The first valve part 44 receives the inflation medium via the inlet 46 and delivers the inflation medium to the outside or to the disposal storage via the outlet 47. The second valve part 45 comprises a plug element 48 insertable into the opening 49 in the first valve part 44 and thereby blocks the passage between the inlet 46 and the outlet 47. The second valve part is connected to or forms a pull tab 50 which can be reached on the outer surface of the apparatus. The user thereby operates the emergency release structure by pulling the pull tab whereby the first and second valve parts separate and the inflation medium drains out of the apparatus or into the disposal storage. As it appears from the description and drawings, the emergency release structure is completely independent on electrical power, i.e. completely non-electrically operated and activation of the emergency release structure prevents further use of the apparatus.

The invention claimed is:

1. A device for thermal ablation at a site in a subject, the device comprising a fluid contained in a reservoir, wherein the reservoir comprises:
   an expandable bladder;
   a displacement chamber having a variable volume;
   an elongated catheter forming fluid communication between the bladder and the displacement chamber; and
   a heater for heating the fluid;
   wherein the displacement chamber comprises a syringe structure including a piston movable in a cylinder by power driven means for varying the volume of the displacement chamber,
   wherein the syringe structure is operable in two directions for reduction and expansion of the volume of the displacement chamber,
   wherein the reservoir is completely sealed, and
   wherein the piston forms a cavity formed to receive the heater when the volume of the displacement chamber is reduced.

2. The device according to claim 1, wherein relative displacement of the cylinder and piston is caused via a threaded engagement between the piston and the power driven means.

3. The device according to claim 1 further comprising a battery connected to power the power driven means and the heater.

4. The device according to claim 1, wherein the heater is controlled to heat the fluid to a temperature in the range 120-150 degrees Celsius.

5. The device according to claim 1, wherein the reservoir comprises an emergency exit for draining the fluid from the reservoir independent on operation of the power driven means.

6. The device according to claim 5, wherein the emergency exit is in fluid communication with a body of a liquid absorbing material.

7. The device according to claim 1, wherein the catheter is formed in one piece with the bladder.

8. The device according to claim 1, wherein the catheter is formed in one piece with one of the cylinder and the piston.

9. The device according to claim 1, further comprising a transition body attached to the catheter and located inside the bladder, the transition body being softer than the catheter.

10. The device according to claim 1, further comprising a sealing member protruding on an outer surface of the catheter and extending circumferentially on an outer surface of the catheter.

11. The device according to claim 10, wherein the sealing member is configured to expand upon contact with the fluid contained in the reservoir.

12. The device according to claim 10, wherein the sealing member is configured to expand based on an increased temperature.

13. The device according to claim 1, wherein the syringe structure is configured to increase the volume of the displacement chamber while the fluid is heated to thereby compensate for an increase in volume of the fluid caused by heating.

14. The device according to claim 1, wherein the apparatus comprises powering means configured to power the heater by a pulsating electrical signal causing a cyclically repeated increase and decrease of the temperature of the heater.

15. The method of manufacturing a device according to claim 1, the method comprising using the power driven means to expand the volume of the chamber prior to, or during sterilisation of the device to thereby counteract volumetric expansion of the fluid caused by heating during the sterilisation.

* * * * *